(12) United States Patent
Wittenberger et al.

(10) Patent No.: US 6,585,717 B1
(45) Date of Patent: Jul. 1, 2003

(54) DEFLECTION STRUCTURE

(75) Inventors: Dan Wittenberger, Pierrefonds (CA); Cristian Petre, Laval (CA); Benoit Thibault, St.-Zotique (CA); Sean Carroll, Beaconsfield (CA)

(73) Assignee: CryoCath Technologies Inc., Kirkland (CA)

( * ) Notice: Subject to any disclaimer, the term of this patent is extended or adjusted under 35 U.S.C. 154(b) by 329 days.

(21) Appl. No.: 09/596,227

(22) Filed: Jun. 15, 2000

Related U.S. Application Data

(60) Provisional application No. 60/139,193, filed on Jun. 15, 1999.

(51) Int. Cl.$^7$ .............................................. A61M 25/00
(52) U.S. Cl. ..................................................... 604/523
(58) Field of Search ................................. 604/523, 524, 604/526, 525, 527, 528, 529, 536, 531, 532, 535

(56) References Cited

U.S. PATENT DOCUMENTS

| | | |
|---|---|---|
| 3,470,876 A | 10/1969 | Barchilon |
| 3,524,446 A | 8/1970 | Crump et al. |
| 3,625,200 A | 12/1971 | Muller |
| 4,456,017 A | 6/1984 | Miles |
| 4,601,705 A | 7/1986 | McCoy et al. |
| 4,738,659 A * | 4/1988 | Sleiman ..................... 600/118 |
| 4,787,399 A | 11/1988 | Bonello et al. |
| 4,930,494 A | 6/1990 | Takehana et al. |
| 4,934,340 A | 6/1990 | Ebling et al. |
| 4,998,923 A | 3/1991 | Samson et al. |
| 5,003,989 A | 4/1991 | Taylor et al. |
| 5,108,368 A | 4/1992 | Hammerslag et al. |
| 5,114,414 A | 5/1992 | Buchbinder |
| 5,135,531 A | 8/1992 | Shiber |
| 5,170,787 A | 12/1992 | Lindegren |
| 5,271,381 A | 12/1993 | Ailinger et al. |
| 5,279,559 A | 1/1994 | Barr |
| 5,308,324 A | 5/1994 | Hammerslag et al. |
| 5,315,996 A | 5/1994 | Lundquist |
| 5,318,041 A | 6/1994 | DuBois et al. |
| 5,318,525 A | 6/1994 | West et al. |
| 5,322,064 A | 6/1994 | Lundquist |
| 5,327,905 A | 7/1994 | Avitall |
| 5,330,466 A | 7/1994 | Imran |
| 5,358,479 A | 10/1994 | Wilson |
| 5,368,564 A | 11/1994 | Savage |
| 5,370,678 A | 12/1994 | Edwards et al. |
| 5,383,852 A | 1/1995 | Stevens-Wright |
| 5,383,923 A | 1/1995 | Webster, Jr. |
| 5,389,073 A | 2/1995 | Imran |
| 5,391,147 A | 2/1995 | Imran et al. |
| 5,437,288 A | 8/1995 | Schwartz et al. |
| 5,441,483 A | 8/1995 | Avitall |
| 5,480,382 A | 1/1996 | Hammerslag et al. |
| 5,484,407 A | 1/1996 | Osypka |
| 5,489,270 A | 2/1996 | van Erp |

(List continued on next page.)

FOREIGN PATENT DOCUMENTS

| | | |
|---|---|---|
| EP | 0605796 A2 | 7/1994 |
| EP | 0790066 A2 | 8/1997 |
| WO | WO 93/20767 | 10/1993 |
| WO | WO 95/10318 | 4/1995 |
| WO | WO 95/10319 | 4/1995 |

*Primary Examiner*—Teresa Walberg
*Assistant Examiner*—Daniel Robinson
(74) *Attorney, Agent, or Firm*—Christopher & Weisberg, P.A.

(57) ABSTRACT

Deflection mechanisms are disclosed that are positionable to deflecting portions of a flexible body, such as a catheter, in more than one direction in a single plane, as well as in more than one plane. The invention allows a distal portion of a catheter to be deflected more than 360 degrees to provide a loop.

15 Claims, 7 Drawing Sheets

U.S. PATENT DOCUMENTS

| | | |
|---|---|---|
| 5,507,725 A | 4/1996 | Savage et al. |
| 5,545,200 A | 8/1996 | West et al. |
| 5,558,665 A | 9/1996 | Kieturakis |
| 5,562,619 A | 10/1996 | Mirarchi et al. |
| 5,571,085 A | 11/1996 | Accisano, III |
| 5,597,378 A | 1/1997 | Jervis |
| 5,603,697 A | 2/1997 | Grundy et al. |
| 5,611,777 A | 3/1997 | Bowden et al. |
| 5,617,854 A | 4/1997 | Munsif |
| 5,619,993 A | 4/1997 | Lee |
| 5,642,736 A | 7/1997 | Avitall |
| 5,645,520 A | 7/1997 | Nakamura et al. |
| 5,656,029 A | 8/1997 | Imran et al. |
| 5,662,621 A | 9/1997 | Lafontaine |
| 5,674,197 A | 10/1997 | van Muiden et al. |
| 5,676,653 A | 10/1997 | Taylor et al. |
| 5,715,817 A | 2/1998 | Stevens-Wright et al. |
| 5,755,760 A | 5/1998 | Maguire et al. |
| 5,807,354 A * | 9/1998 | Kenda ......................... 604/174 |
| 5,820,591 A * | 10/1998 | Thompson et al. .......... 604/529 |
| 5,865,800 A | 2/1999 | Mirarchi et al. |
| 5,882,329 A * | 3/1999 | Patterson et al. ............ 604/500 |
| 5,891,088 A | 4/1999 | Thompson et al. |
| 5,916,178 A | 6/1999 | Noone et al. |
| 5,931,811 A | 8/1999 | Haissaguerre et al. |
| 6,002,955 A | 12/1999 | Willems et al. |
| 6,033,394 A * | 3/2000 | Vidlund et al. .............. 138/172 |
| 6,045,530 A * | 4/2000 | Krueger et al. .............. 604/524 |
| 6,066,125 A | 5/2000 | Webster, Jr. |
| 6,110,164 A * | 8/2000 | Vidlund ....................... 604/524 |

\* cited by examiner

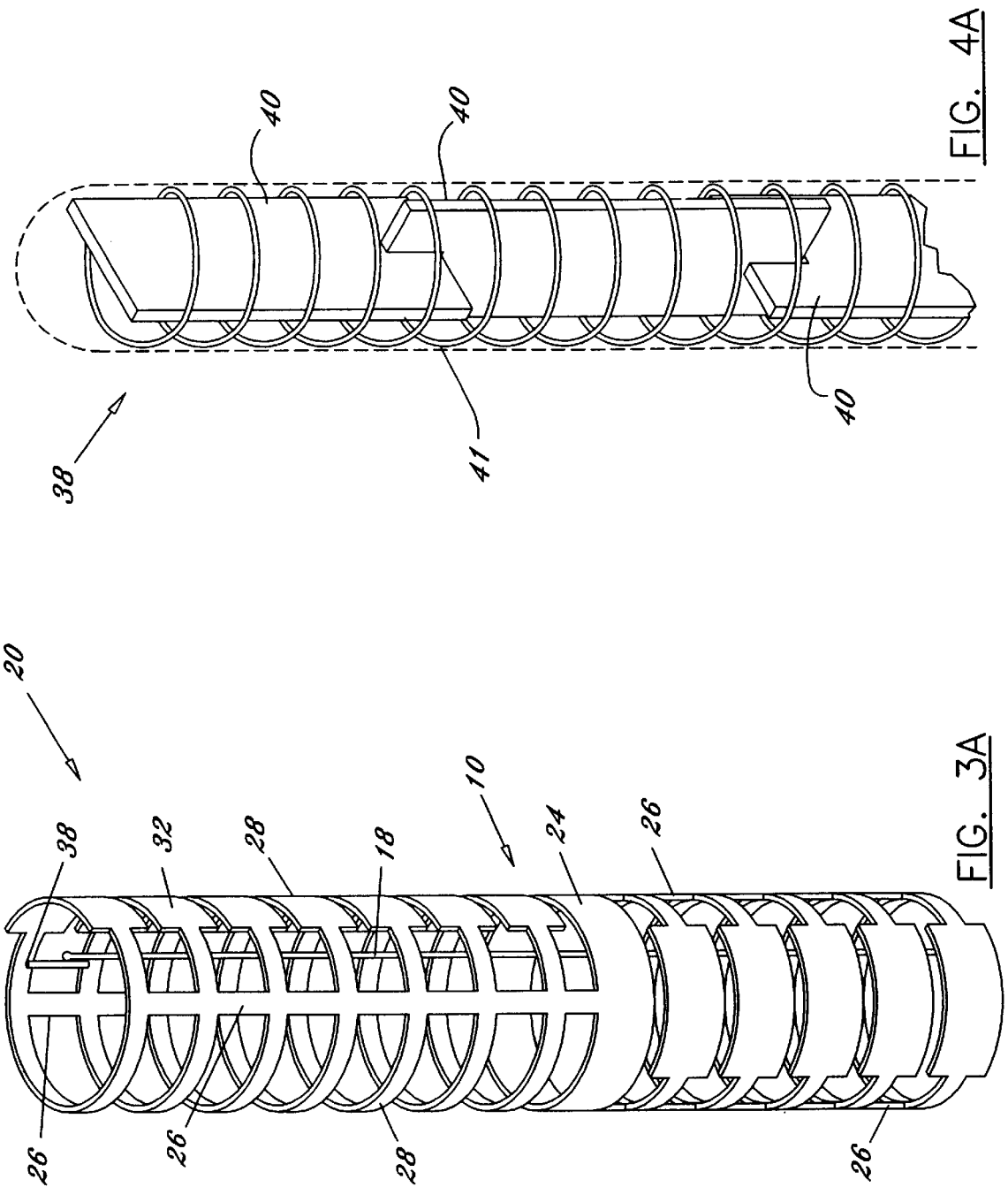

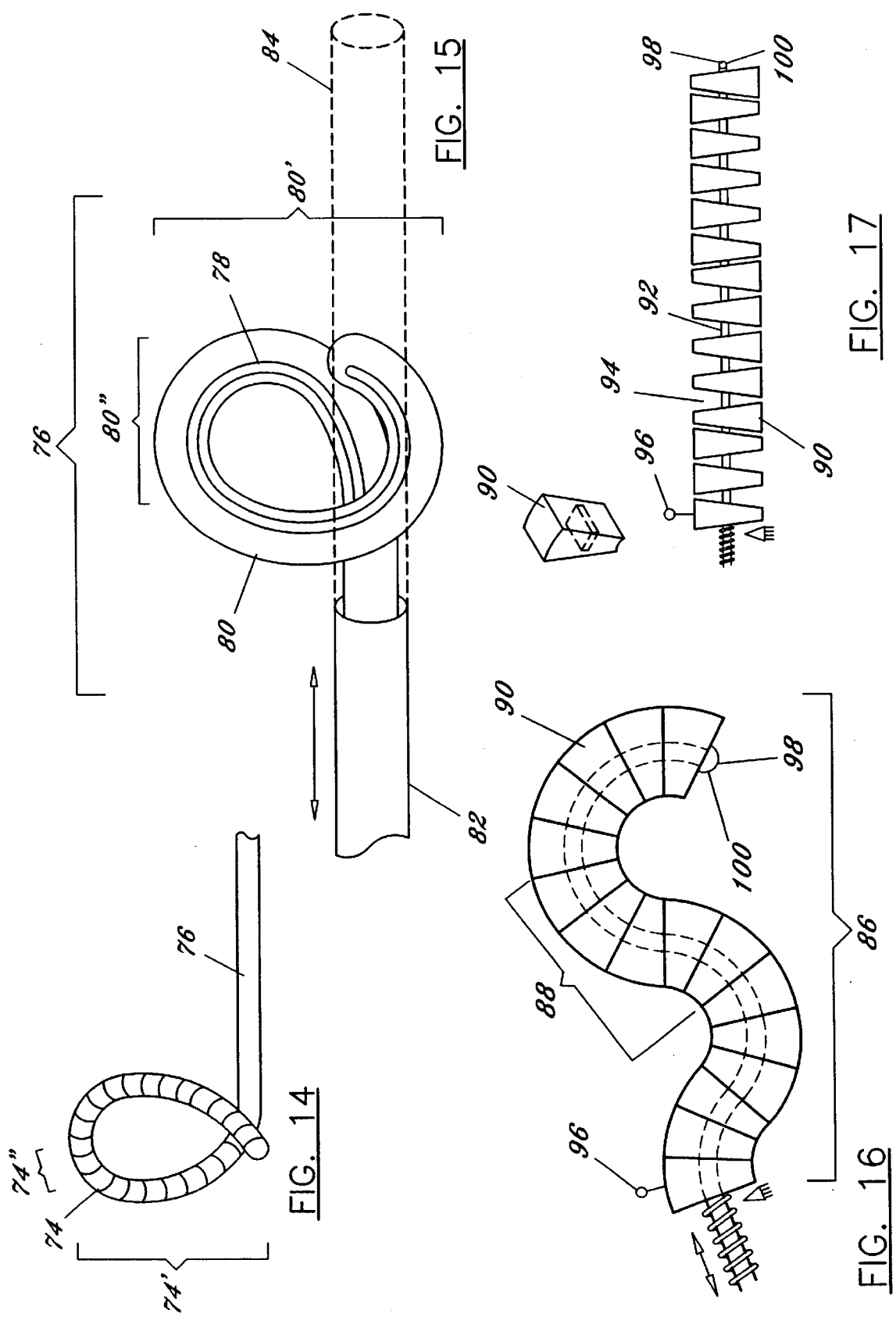

DEFLECTION STRUCTURE

CROSS-REFERENCE TO RELATED APPLICATIONS

This application claims priority from U.S. Provisional Patent Application Serial No. 60/139,193, filed Jun. 15, 1999.

STATEMENT REGARDING FEDERALLY SPONSORED RESEARCH

Not applicable.

FIELD OF THE INVENTION

The present invention relates to medical devices, and more particularly to steerable catheters.

BACKGROUND OF THE INVENTION

Minimally invasive surgery is commonly performed by inserting relatively small instruments into the body, as well as organs within the body, through one or more very small incisions. Many instruments are rigid and are directed to a site of interest by angling the instrument through the incision and inserting the device to a selected depth within the body. However, rigid instruments are unacceptable for many procedures, and even less invasive procedures have been developed that employ flexible catheter-based instruments. Although early catheter devices simply followed the contours of a body passage, such as a blood vessel to a selected treatment site, catheters with movable tip portions were developed to provide simple catheter steering.

The present steerable catheters most commonly include one or more wires that are anchored at a first point near the distal tip of the catheter and at a second point at the proximal end of the catheter or in a handle unit. A lever or knob is actuated to apply or reduce tension on the one or more wires causing the distal tip of the catheter to be pulled in the direction of the tension. Although steering mechanisms such as these have provided excellent results, it is believed that even greater steering or deflection control would further increase the possibilities for new surgical procedures, It would be especially desirable if existing and well developed pull-wire technology could be employed with new structures to provide such enhanced capability.

SUMMARY OF THE INVENTION

The present invention overcomes the limitations of known pull-wire steering mechanism to provide a deflection mechanism capable of deflecting portions of a flexible body, such as a catheter, in more than one direction in a single plane, as well as in more than one plane. The invention allows a distal portion of a catheter to be deflected more than 360 degrees to provide a loop.

In an exemplary embodiment, a deflection mechanism for a medical device includes rings and a connecting structure connecting the rings. The connecting structure can include a unitary structure or rod segments that connect adjacent rings. A second connecting structure can be provided that is radially spaced apart from the first connecting structure. A second group of rings, joined by another connecting mechanism can be provided so that the first rings deflect in a first plane and the second rings deflect in a second plane.

In another embodiment, a deflection mechanism for a medical device includes three planar shims defining three planes. Adjacent planar shims are joined so that the planes defined by each respective shim are different.

Yet another embodiment of a deflection mechanism for a medical device includes a deflection body having a longitudinal axis and two pairs of longitudinal elements secured to the deflection body at different locations.

Still another embodiment of the invention includes a catheter having a distal end and a pair of helically twisted elements extending longitudinally through the catheter proximate the distal end.

Another embodiment of the invention includes a catheter, a shape biased member disposed within the catheter, and a sheath slidably disposed over the catheter.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 3A is a perspective view of an embodiment of a deflection structure of a catheter in accordance with the invention;

FIG. 4A is a perspective view of another embodiment of a deflection structure of a catheter in accordance with the invention;

FIG. 14 is a perspective view of another embodiment of a deflection structure of a catheter in accordance with the invention shown in an actuated multi-plane state;

FIG. 15 is a partial cross-sectional view of another embodiment of a catheter in an actuated multi-plane state in accordance with the invention;

FIG. 16 is a side view of another embodiment of a deflection structure of a catheter in accordance with the invention in an actuated multi-plane state;

FIG. 17 is a side view of the embodiment of FIG. 16 shown in a non-actuated state;

DETAILED DESCRIPTION OF THE INVENTION

The inventive deflection features disclosed herein have applicability to any flexible body, such as a catheter-based surgical device and references to specific systems or procedures are merely exemplary.

Figure 1A:
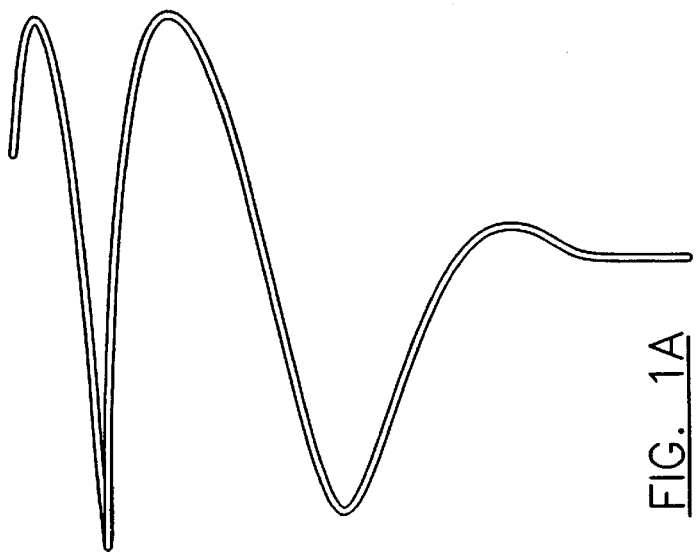
FIG. 1A is a side view of a deflected catheter body in accordance with the invention.
Figure 1B:
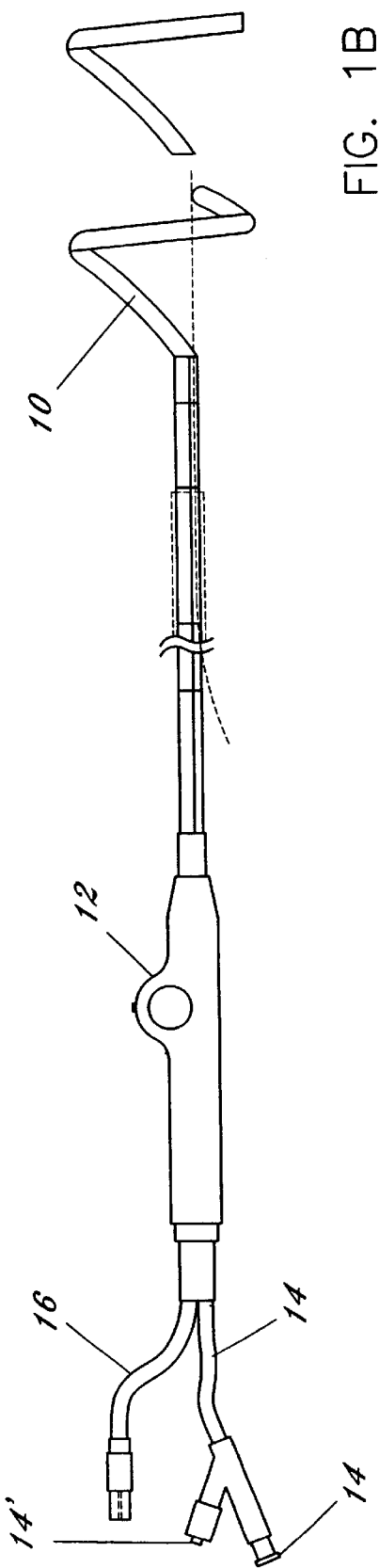
FIG. 1B is a side view of a catheter system in accordance with the invention.

FIG. 1B shows a catheter system in accordance with the invention. The system includes a catheter body 10 that is shown in an actuated or deflected state or condition. In this illustration, the catheter is configured so that the distal region of the catheter body 10 deflects in more than one plane to provide a "cork-screw" or helical tip region. Although a screw shape is shown, the catheter can be configured to provide other complex configurations. It should also be understood that the catheter can be actuated and used though a range of deflections at points other than a maximally deflected configuration. In other words, the system is not simply a two-state system (no deflection/full deflection).

FIG. 1A illustrates a catheter body 10 having multiple loops, wherein the distal end of the catheter is deflected well in excess of 360 degrees.

Deflection structures or mechanisms for the present catheter system are described in greater detail below, and are compatible for use with catheters such as those disclosed in U.S. Pat. Nos. 5,899,898 and 5,899,899 to Arless et al., which are incorporated herein by reference.

Continuing to refer to FIG. 1B, the system also includes a handle 12. First and second umbilicals 14 and 16, respectively, can be provided to connect the handle 12 to a console (not shown) that supports the surgical function of the selected device. For example, the first umbilical 14 can provide a path for a liquid or gas refrigerant to be transferred between the console and the handle 12; and the second umbilical 16 can provide a signal path, such as for electrical signals, between the console and the handle. Additional umbilicals can be provided as required, and the functions of more than one umbilical can be provided in a single, multifunction umbilical. Also, one or more of the umbilicals can be divisible into two or more portions as shown in FIG. 1B, wherein the first umbilical includes portion 14 and 14'.

Figure 2:
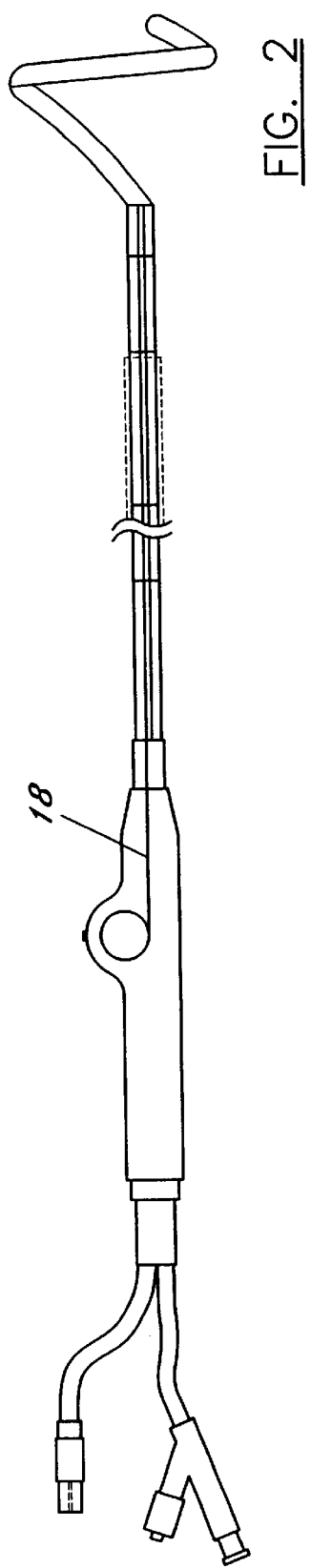
FIG. 2 is a side view of another catheter system in accordance with the invention.

FIG. 2 depicts an exemplary embodiment as shown in FIG. 1 which further includes a pull-wire 18. Although the present invention can use pull-wires to cause deflection, as discussed below, additional structures are provided that cause the deflection to produce a shape other than a simple, single plane bend. Further, although a pull-wire(s) can be used to cause deflection, the disclosed structures can be associated with other movement mechanisms to provide the inventive configurations.

Referring now to FIG. 3A, additional details of an exemplary deflection structure or mechanism are discussed in greater detail. A catheter body 10 is shown in a deconstructed view so that a deflection structure 20 can be more easily understood. The deflection structure 20 comprises a tip 22 connected to an intermediate point 24 by a connecting structure, which forms a distal deflection group. In this embodiment the connecting structure includes first and second flexible connecting rods 26. Disposed along connecting rods 26 are multiple rings 28, each defining a plane. Each ring 28 is aligned with a plane that is substantially perpendicular to a longitudinal axis of the connecting rods 26 when in a non-actuated state as shown in FIG. 3A. Connecting rods 26 can also be represented by a plurality of rod segments that connect rings 28. Additionally, a pull-wire 18 is disposed within the deflection structure 20. Referring now to an enlarged view in FIG. 3B, the asymmetrical rings 28 have a first half 32 and a second half 34. The first half 32 includes a flattened, curved portion or shaped spine section 36.

Figure 3C:
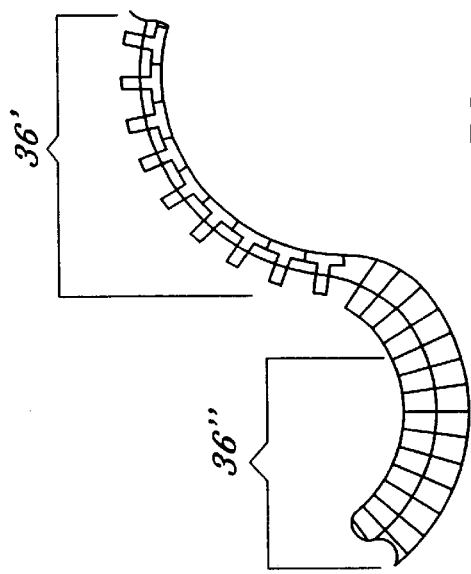
FIG. 3C is a perspective view of an aspect of the embodiment of a deflection structure shown in FIG. 3A of a catheter in accordance with the invention shown in an actuated multi-plane state.
Figure 3B:
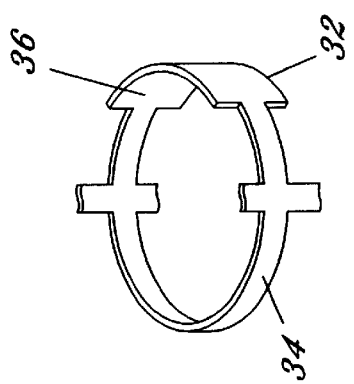
FIG. 3B is a perspective view of an aspect of the embodiment of FIG. 3A in accordance with the invention.

Referring again to FIG. 3A, operation of the device is now discussed. Tension is applied to the pull-wire 18, which is attached at a point 38 in the tip 22, thereby causing the deflection structure 20 to bend toward the first half 32 of the rings 28. The tension can be applied until a full actuation state occurs and the individual spine sections 36 contact one another as shown in FIG. 3C. In the full actuation state the deflection structure 20 takes a pre-determined shape that is defined by the specific physical construction of the individually shaped spine sections 36 to define a first deflection plane. Additionally, more shaped spine sections 36 may be located proximal to the intermediate point 24 with a similar arrangement as described above, further defining a second deflection plane, which is different than the first deflection plane. The first and second deflection planes are aligned radially different from one another. FIG. 3C shows the first deflection plane 36' and the second deflection plane 36".

Figure 3D:
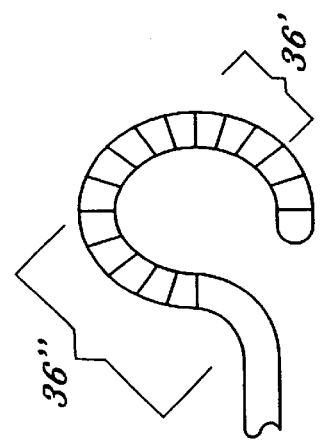
FIG. 3D is a perspective view of an embodiment of a deflection structure in an actuated multi-plane state in accordance with the invention.

Additional discrete deflection structure sections can be added to the catheter tip to form other desired deflection shapes. An exemplary resultant shape of the catheter body in a full actuation state is shown in FIG. 3D. Shown are the first deflection plane 36' and the second deflection plane 36".

The above described structure may be formed from one piece of material or from multiple pieces and then secured together by methods known in the art. For example, a one piece assembly can be manufactured using a laser machining The material can be a super-elastic spring steel, a polymer or any other suitable material.

Turning now to FIG. 4A, another exemplary embodiment of a deflection structure for a catheter is shown and discussed in greater detail. Shown is a deflection structure 38 having first, second and third planar shims 40. Each planar shim 40 is a flat elongate piece of material with ends, and that define discrete planes. Each of the planar shims 40 are joined to one another at their ends and are aligned in a different plane relative to each other. When actuated, each of the deflection shims will bend in a deflection plane that is substantially perpendicular to the shim's plane and will form a pre-determined actuation shape. Further, a coil 41 can be disposed around at least a portion of the joined planar shims 40.

Figure 4B:
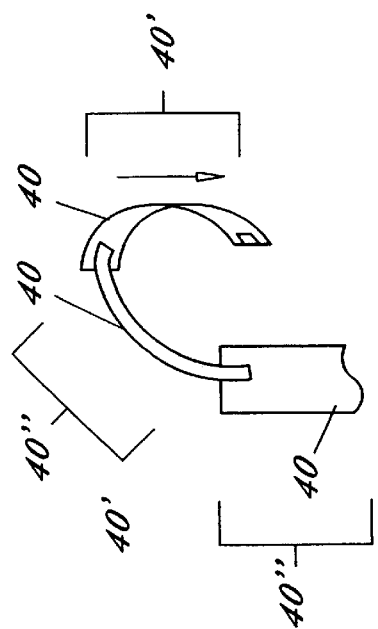
FIG. 4B is a deconstructed perspective view of the embodiment of FIG. 4A in an actuated multi-plane state in accordance with the invention.

For example, FIG. 4B shows a deconstructed view of the deflection structure of FIG. 4A in an actuated state, planar shims 40 are each actuated in a separate plane. Shown is a first deflection plane 40', a second deflection plane 40" and a third deflection plane 40'". The actuation of the deflection shims 40 can be accomplished by one or more pull-wires disposed within the deflection mechanism and attached at various locations to effect different final and intermediate configurations. The planar shims 40 can be joined in many different ways, for example, they may be slotted and fitted together or they may be welded together. The planar shims can be constructed from a spring material and actuation may be accomplished by applying tension supplied by one or more pull-wires, or by constructing the planar shims from a shape-memory material and applying that materials' required means, as is known in the shape-memory art. For example, inducing a temperature change in the material can cause it to assume a preset shape.

Figure 5:
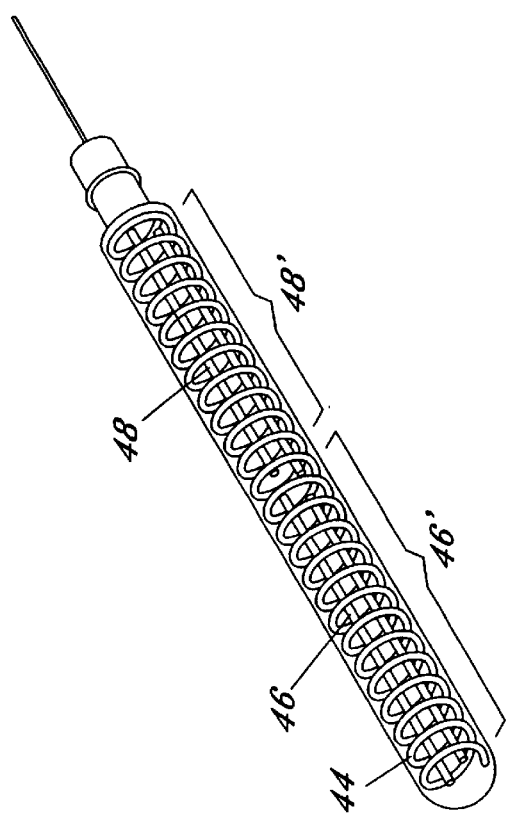
FIG. 5 is a perspective view of another embodiment of a deflection structure of a catheter in accordance with the invention shown in a non-actuated state.

Turning now to FIG. 5, another exemplary embodiment of a deflection structure for a catheter is shown and discussed in greater detail. Shown is a deflection body 42. Disposed within an optional helical coil 44 are a first pair 46 and second pair 48 of longitudinal elements arranged substantially parallel to a longitudinal axis of deflection body 42. The helical coil 44 helps to maintain a relatively straight configuration of the deflection structure when in a non-actuated state. The first pair 46 and second pair 48 of longitudinal elements each define an independent plane of deflection, a first deflection plane 46' and a second deflection plane 38' respectively, when actuated. A junction 50 defines the relative radial angle of alignment of the pairs of longitudinal elements.

Figure 7:
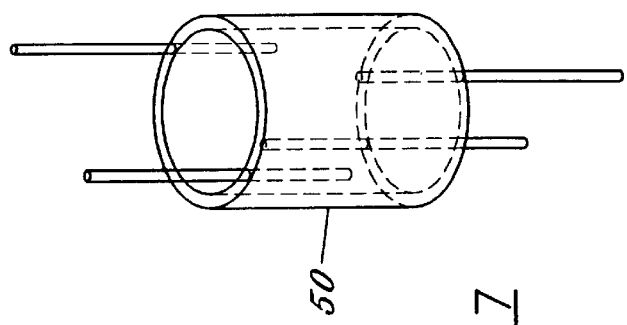
FIG. 7 is a view of a coupling in accordance with the invention.
Figure 8:
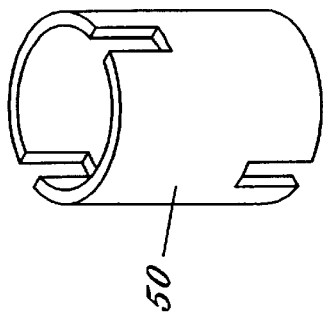
FIG. 8 is an exploded view of another coupling in accordance with the invention.

FIG. 7 and FIG. 8 show detailed views of a junction 50 that can be used to join the first and second pairs of longitudinal elements at different radial angles relative to one another. The longitudinal elements can be manufactured from a spring material and actuation can be accomplished by applying tension with one or more pull-wires, or by constructing the longitudinal elements from a shape-memory material and applying that materials' required means, such as temperature.

Figure 6:
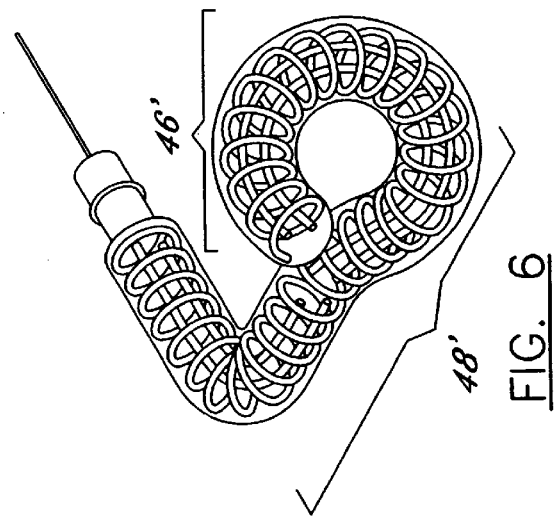
FIG. 6 is a perspective view of an embodiment of a deflection structure of a catheter in accordance with the invention shown in an activated state.

FIG. 5 shows the deflection structure 42 in a non-actuated state. When the deflection structure is actuated it assumes a pre-determined shape, for example, as shown in FIG. 6.

Figure 9:
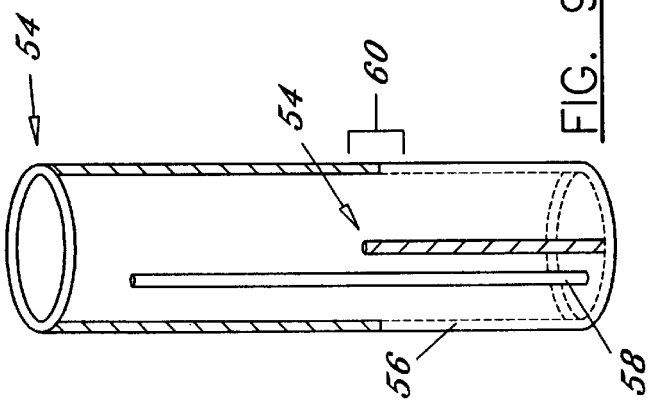
FIG. 9 is a partial cross-sectional view of another embodiment of a deflection structure of a catheter in accordance with the invention.

Turning now to FIG. 9, another exemplary embodiment of a deflection structure for a catheter is shown and discussed in greater detail. This embodiment comprises a series of longitudinal elements 54 embedded or attached to a flexible tube 56. The longitudinal elements 54 are constructed of a spring material or a shape-memory material. When tension is applied to a pull-wire 58 or alternatively when the actuating mechanism of the shape memory material is applied, the longitudinal elements 54 deflect in different planes to assume an actuation state as shown in FIG. 14. The relative radial angle of multiple pairs of longitudinal elements 54 can be controlled to specifically define final or intermediate actuation state shapes according to application demands.

Figure 11:
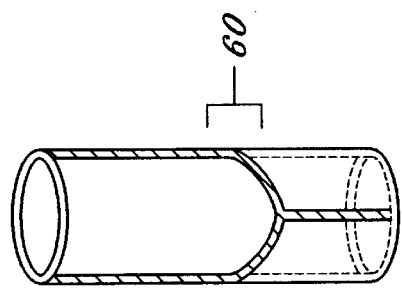
FIG. 11 is a partial cross-sectional view of another embodiment of a deflection structure of a catheter in accordance with the invention.
Figure 10:
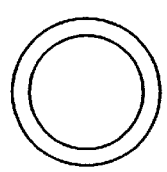
FIG. 10 is a sectional end view of an embodiment of a deflection structure of a catheter in accordance with the invention.

Different embodiments of a transition zone 60 can be seen in FIGS. 9, 10 and 11. Transition from one plane to another can be immediate or gradual. Further, a junction 50 as seen in FIGS. 7 and 8 can be used.

Figure 12:
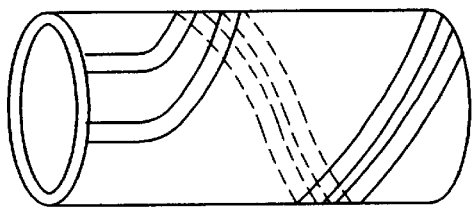
FIG. 12 is a partial cross-sectional view of another embodiment of a deflection structure of a catheter in accordance with the invention.

Additionally, as seen in FIG. 12, a coiled element pair 62 can be used to create an uncoiling action upon actuation resulting in an actuation state as seen in FIG. 14. Again, the final actuation state can be predetermined to suit application demands by the manufacturer.

Figure 13:
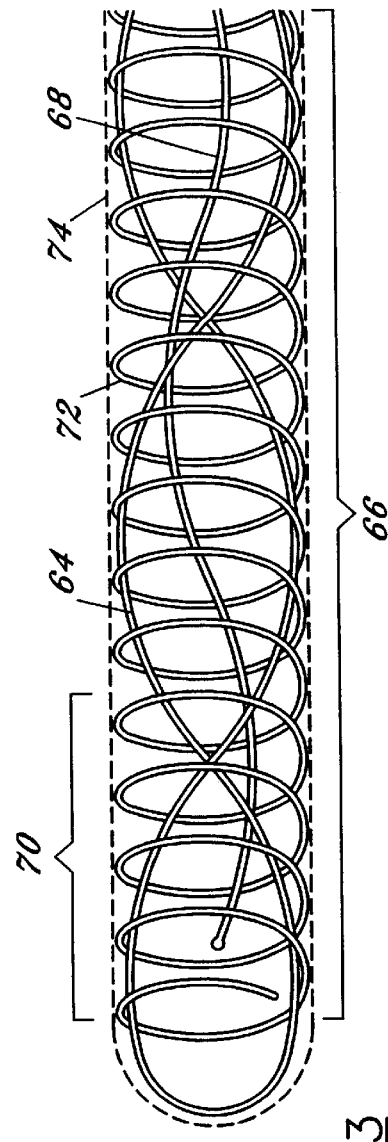
FIG. 13 is a partial cross-sectional view of another embodiment of a catheter in accordance with the invention.

Shown in FIG. 13, is a pair helically twisted elements 64 having a continuous helical-shaped twist contained inside a deflection body 66. A pull-wire 68 is attached to a distal end 70 of the deflection body 66. A wire coil 72 encloses the assembly and supports a membrane 74. The coil 72 prevents the pull-wire 68 from "straightening" when in a non-actuated state. When a pull tension is applied to the pull-wire 68, the struts 64 are deflected in a plane perpendicular to the struts, in a continuously rotating direction. The final shape of the distal end 70 is a ring 74 configured perpendicular to the catheter shaft 76, as seen in FIG. 14. The plane in which the distal end 70 moves to the ring 74 can be made to be in a plane perpendicular to the shaft, depending on the pitch and number of twists. FIG. 14 shows a first deflection plane 74' and a second deflection plane 74".

Turning now to FIG. 15, another exemplary embodiment of a deflection structure for a catheter is shown and discussed in greater detail. The deflection structure 76 comprises a shape biased member 78 included in a distal section of a catheter tip 80, and a sheath 82 that houses the catheter tip 80 until the place and time of actuation. The shape biased member 78 has a pre-determined shape and can be reversibly conformed to a non-actuated state 84 by sliding the sheath 82 over it. When the sheath 82 is partially withdrawn from the catheter tip 80 or the catheter tip 80 is advanced relative to the sheath 82, the shape biased member 78 assumes its pre-determined shape and is thus actuated. The shape biased member 78 may be made of polymer, a spring-tempered stainless or super-elastic alloy that when released from the sheath 82 will force the catheter tip 80 to take the shape desired. FIG. 15 shows a first deflection plane 80' and a second deflection plane 80".

Another embodiment as disclosed in FIG. 16 shows a deflection structure 86 which comprises a plurality of curves 88 with a pre-established deflection shape. Turning to FIG. 17, a series of beveled-faced elements 90 are placed over one or more wires 92 (either rectangular section wire or a pair of round wires). Initially the beveled-faced elements 90 are free-floating on the wires 92, with small intervals 94 in between each element 90. When a pull tension is applied to the wires 92, a first element 96 will be pressed against a fixed point 98 at the deflection structure tip 100, and subsequently each of the remaining elements 90 will be pulled close together until all the beveled facets are in contact with one another, thereby imparting a specific angular abutment to the catheter tip in a pre-established shape. The pre-established shape depends on the sequence of angles on the faces of the elements and their predetermined configuration. FIG. 16 shows an exemplary actuation shape.

Figure 18:
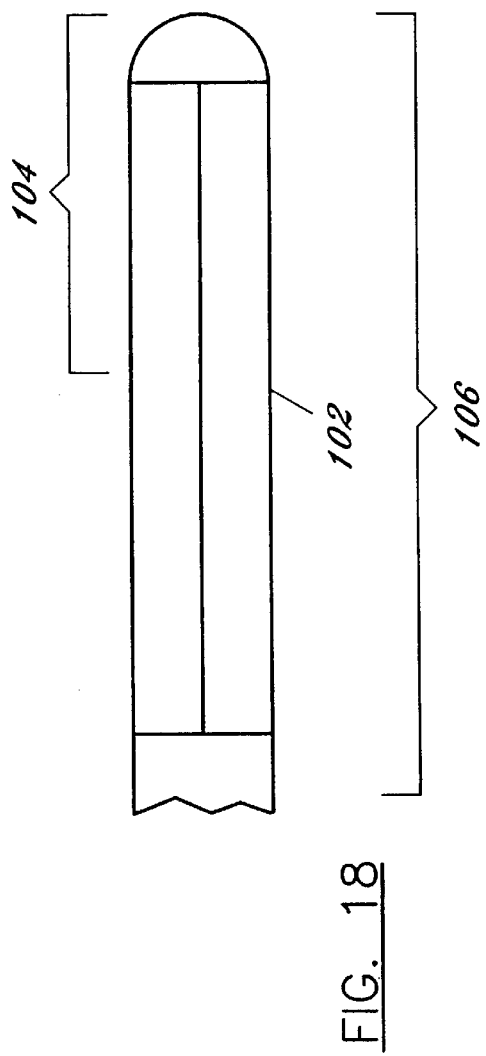
FIG. 18 is a side view of another embodiment of a deflection structure of a catheter in accordance with the invention, shown in a non-actuated state.
Figure 19:
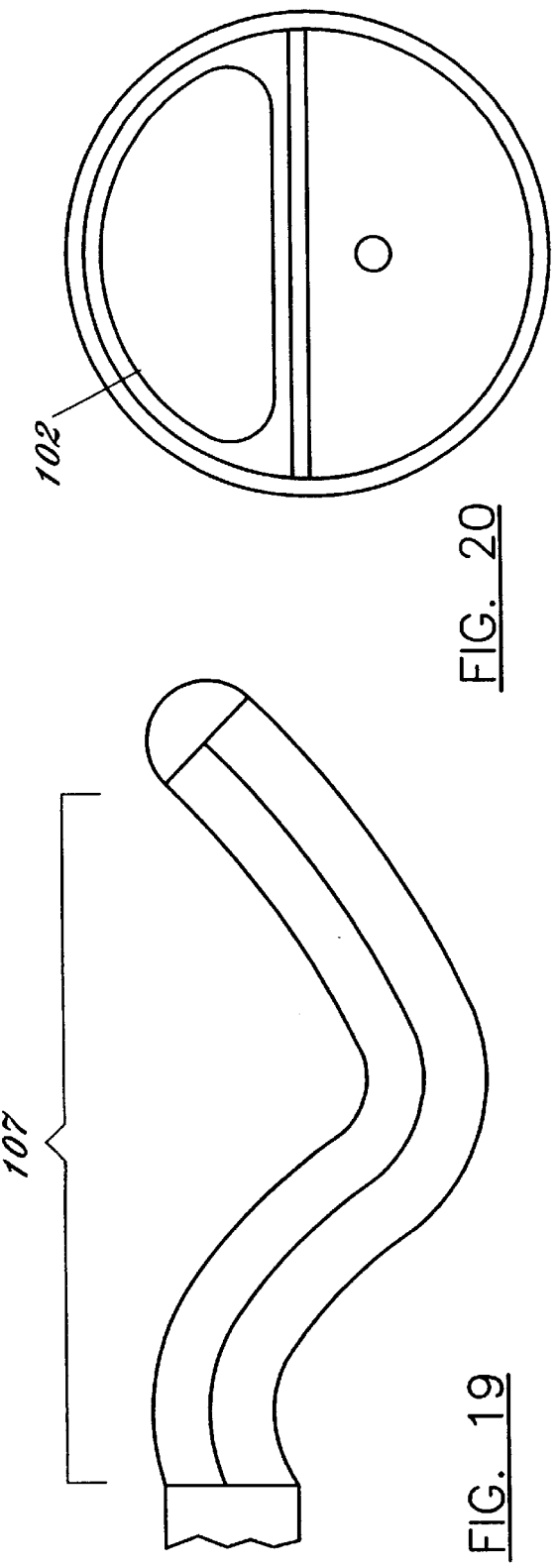
FIG. 19 is a side view of the embodiment shown in FIG. 18, shown in an actuated multi-plane state.
Figure 20:
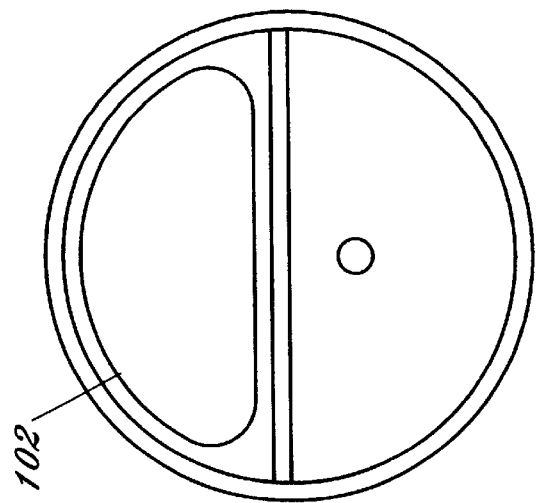
FIG. 20 is an end cross-sectional view of the embodiment shown in FIGS. 18 and 19.

Another exemplary embodiment as shown in FIG. 18 comprises a preformed balloon insert 102 placed in a distal segment 104 of a catheter tip 106 which upon inflation conforms the catheter tip to a predetermined profile 107 as seen in FIG. 19. Additionally, the preformed balloon insert 102 acts as an insulation material. The preformed balloon insert 102 is constructed from a non-compliant balloon that is preformed by blow-molding and/or thermally setting or by other suitable means to a defined shape. The preformed balloon insert 102 is housed in a distal end of a catheter 10 as seen in FIG. 1. After being placed close to the target tissue, the preformed balloon insert 102 is inflated with a non-compressible, biocompatible liquid through an inflation lumen (not shown). The preformed balloon insert 102 will force the catheter tip 104 to take its shape. The preformed balloon insert 102 has a triple role, shaping the tip, increasing rigidity, and shielding the catheter's dorsal side from unwanted heat.

A variety of modifications and variations of the present invention are possible in light of the above disclosure. It is therefore understood that, within the scope of the appended claims, the present invention may be practiced otherwise than as specifically described hereinabove.

What is claimed is:

1. A deflection mechanism for a medical device comprising:
   a plurality of rings; and
   a connecting structure connecting the plurality of rings, wherein the plurality of rings are aligned with a plane that is substantially perpendicular to a longitudinal axis of the connecting structure when in a non-actuated state.

2. The deflection mechanism of claim 1, wherein the connecting structure includes a plurality of rod segments that connect adjacent rings.

3. The deflection mechanism of claim 2, wherein the plurality of rod segments are axially aligned.

4. The deflection mechanism of claim 2, wherein not all of the rod segments are axially aligned.

5. The deflection mechanism of claim 1, wherein the connecting structure is a unitary element.

6. The deflection mechanism of claim 1, wherein the plurality of rings are of uneven thickness.

7. The deflection mechanism of claim 6, wherein approximately one half of each ring includes a flattened, curved portion.

8. The deflection mechanism of claim 7, further comprising a second connecting structure connecting the plurality of rings, wherein the second connecting structure is radially spaced apart from the first connecting structure.

9. The deflection mechanism of claim 8, wherein the flattened, curved portion of each ring is bounded by the first and second connecting structures.

10. The deflection mechanism of claim 1, further comprising:
    a second plurality of rings disposed adjacent the first plurality of rings in axial alignment therewith; and
    a second connecting structure connecting the second plurality of rings.

11. The deflection mechanism of claim 10, wherein the first plurality of rings are joined to the second plurality of rings.

12. The deflection mechanism of claim 11, wherein the first connecting structure and the second connecting structure are secured to first plurality of rings and the second plurality of rings, respectively, at different radial locations.

13. The deflection mechanism of claim 10, wherein the first plurality of rings deflects in a first plane and the second plurality of rings deflects in a second plane.

14. A deflection mechanism for a medical device comprising:
    a first planar shim defining a first plane;
    a second planar shim joined to the first planar shim, the second planar shim defining a second plane; and
    a third shim joined to the second planar shim, the third planar shim defining a third plane;
    wherein adjacent planar shims are joined so that the planes defined by each respective shim are different.

15. The deflection mechanism of claim 14, further comprising a coil disposed around at least a portion of the joined shims.

* * * * *